United States Patent
Chandrasekaran et al.

(10) Patent No.: US 6,394,956 B1
(45) Date of Patent: May 28, 2002

(54) RF ABLATION AND ULTRASOUND CATHETER FOR CROSSING CHRONIC TOTAL OCCLUSIONS

(75) Inventors: Chandru V. Chandrasekaran, Mercer Island; Zihong Guo, Bellevue, both of WA (US); Anthony J. Pantages, Los Altos; Donald Masters, Sunnyvale, both of CA (US); Ryan Kaveckis, Seattle, WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/514,970

(22) Filed: Feb. 29, 2000

(51) Int. Cl.[7] .................................................. A61B 8/00
(52) U.S. Cl. ........................ 600/439; 600/466; 607/122
(58) Field of Search ................................. 600/439, 437, 600/459, 462, 463, 466, 467, 469, 470, 471; 607/122; 128/898

(56) References Cited

U.S. PATENT DOCUMENTS

| | | |
|---|---|---|
| 5,000,185 A | 3/1991 | Yock |
| 5,024,234 A | 6/1991 | Leary et al. |
| 5,054,492 A | 10/1991 | Scribner et al. |
| 5,314,438 A | 5/1994 | Shturman |
| 5,454,809 A | 10/1995 | Janssen |
| 5,588,432 A | 12/1996 | Crowley |
| 5,599,346 A | 2/1997 | Edwards et al. |
| 5,626,576 A | 5/1997 | Janssen |
| 5,680,860 A | 10/1997 | Imran |
| 5,683,366 A | 11/1997 | Eggers et al. |
| 5,740,808 A | 4/1998 | Panescu et al. |
| 5,749,914 A | 5/1998 | Janssen |
| 5,817,092 A | 10/1998 | Behl |
| 5,848,969 A * | 12/1998 | Panescu et al. ............. 600/462 |
| 5,967,984 A * | 10/1999 | Chu et al. .................... 600/439 |
| 6,032,673 A * | 3/2000 | Savage et al. .............. 128/989 |
| 6,165,127 A * | 12/2000 | Crowley ...................... 600/463 |

FOREIGN PATENT DOCUMENTS

| | | |
|---|---|---|
| WO | WO 90/07303 | 7/1990 |
| WO | WO 97/45157 | 12/1997 |

\* cited by examiner

Primary Examiner—Marvin M. Lateef
Assistant Examiner—Ali M. Imam
(74) Attorney, Agent, or Firm—Christensen O'Connor Johnson Kindness PLLC

(57) ABSTRACT

A combination catheter includes an ultrasound transducer and RF ablation electrode. The ultrasound transducer transmits ultrasound signals into and receives echo signals from a vessel. The echo signals are processed and used to produce an image of the tissue surrounding the catheter. A driveshaft rotates the ultrasound transducer to obtain a 360° view of the vessel wall. At the distal end of the driveshaft is an electrode. An RF generator is electrically coupled to the driveshaft to deliver RF energy to the electrode at the distal end of the driveshaft to ablate occluding material in the vessel. The electrode may have a variety of tip shapes including concave, roughened, or expandable configurations, depending on the size of the vessel and composition of the occluding material to be ablated. Alternatively, the RF ablation energy may be delivered to a guidewire that is used to route the ultrasound catheter through a patient's vasculature. Finally, a steerable catheter can be used to further position the ultrasound catheter and ablation electrode in the vessel.

7 Claims, 5 Drawing Sheets

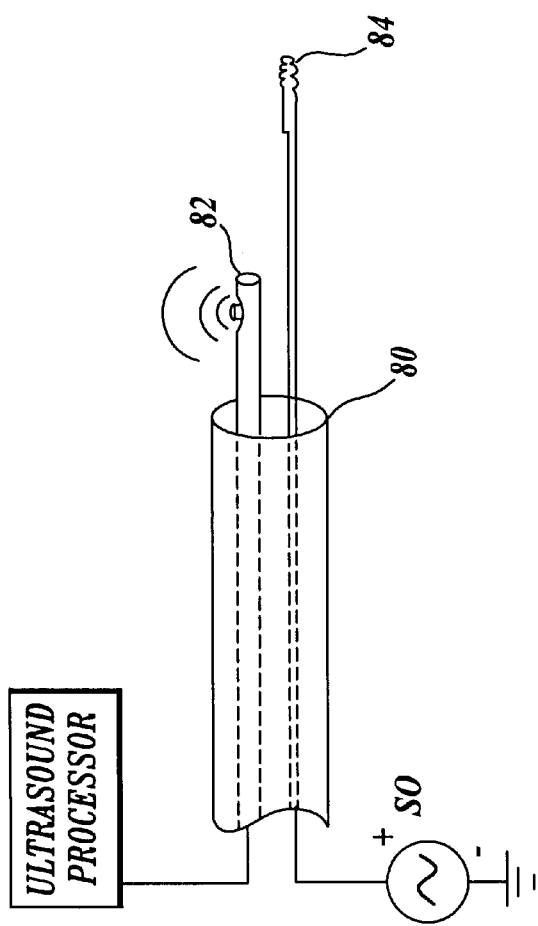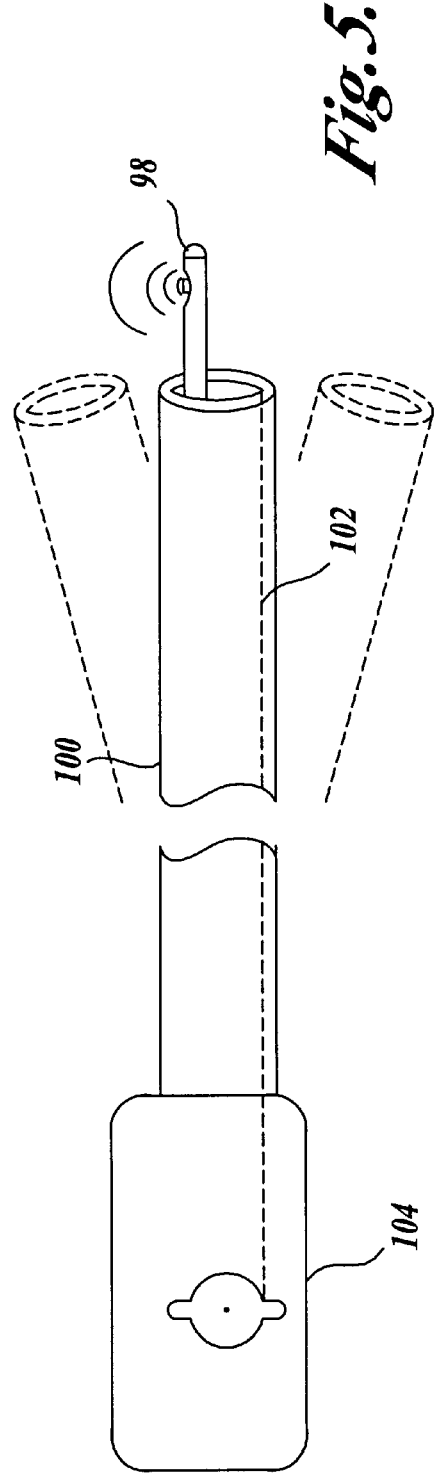

RF ABLATION AND ULTRASOUND CATHETER FOR CROSSING CHRONIC TOTAL OCCLUSIONS

FIELD OF THE INVENTION

The present invention relates to medical devices in general, and in particular to catheter ablation systems for revascularizing occluded vessels.

BACKGROUND OF THE INVENTION

One common form of vascular disease is characterized by deposits that form in a patient's arteries or veins. Once such blockages form in cardiac arteries, they are a significant factor in the occurrence of heart attacks.

In addition to cardiac bypass surgery, new less-invasive techniques such as balloon angioplasty or rotational ablation are being used to treat occluded vessels. In the case of rotational atherectomy, a high speed abrasive burr is routed through the patient's vasculature to the point of the occlusion and used to bore a new lumen through the occlusion in order to restore blood flow. The success of balloon angioplasty and rotational ablation often depends on the nature of the material blocking the vessel. These techniques generally work best when the material is not highly calcified or does not completely occlude the vessel. Total chronic occlusions are typically characterized by a hard calcified material that completely seals off blood flow in a vessel. Some success has been achieved in treating these blockages by advancing a flexible guidewire to the point of the occlusion and "pecking" at the occlusion to create a pathway through it. The problem with the guidewire technique is that it is time-consuming and presents a risk of vessel perforation if the guidewire becomes misaligned.

Given the fact that total chronic occlusions account for between 20–25% of all occlusions treated, there is a need for a system that employs a more aggressive ablation mechanism to reduce the treatment time but reduces the likelihood that the ablation mechanism will become misaligned in the patient's vessel in order to provide an effective method of treating this type of vessel blockage.

SUMMARY OF THE INVENTION

To treat total chronic occlusions, the present invention is a combination ultrasound and ablation catheter that provides a physician with an image of the position of the catheter in the vessel and an image of the occluding material. An ultrasound transducer is located at the distal end of a catheter which generates ultrasound signals and receives corresponding echo signals from the tissue. The echo signals are transmitted to an ultrasound processor which produces an image of the vessel. The catheter is rotated by a driveshaft in order to provide a 360° view of the vessel. In one embodiment of the invention, the ultrasound transducer in the catheter is set at an angle such that echo signals are received from a position slightly ahead of the distal end of the catheter.

To create a new lumen in the vessel, radio frequency (RF) ablation energy is transmitted to an electrode that is located at a distal tip of the combination catheter. The RF energy ablates a portion of the occluding material to create a new lumen in the vessel. In one embodiment of the invention, the ultrasound transducer is rotated by a conductive driveshaft. The electrode is electrically coupled to the driveshaft and the RF energy is applied to the driveshaft to be transmitted to the occlusion The conductive driveshaft is surrounded by a non-conductive sheath. The electrode extends out the distal end of the non-conductive sheath such that RF ablation energy is directed from the exposed electrode and into the occluding material.

According to another aspect of the present invention, the electrode at the distal end of the ultrasound catheter may have a variety of shapes including a concave shape, a convex, hemispherical shape with a roughened outer surface or an expandable tip made of a series of braided wires.

In another embodiment of the invention, the catheter system includes an ultrasound catheter having an ultrasound transducer that is rotated by a driveshaft to obtain images of the vessel and occluding material. The ultrasound catheter is routed in one lumen of a multi-lumen catheter. In another lumen of the multi-lumen catheter is a conductive guidewire. RF ablation energy is applied to the conductive guidewire to ablate the occluding material in the vessel.

In accordance with yet another aspect of the invention, the combination ultrasound and RF ablation catheter is routed through a steerable sheath in order to further aid in the placement of the catheter within the vessel. Alternatively, the electrode that delivers the RF ablation energy is incorporated into the steerable sheath, wherein the ultrasound catheter extends through a hole in the electrode at the distal end of the sheath to obtain images of the vessel and occluding material.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4 illustrates an embodiment of the invention in which RF ablation energy is applied to occluding material in a vessel via a conductive guidewire;

FIG. 5 illustrates the use of a steerable sheath through which an RF ablation and ultrasound catheter are routed;

DETAILED DESCRIPTION OF THE PREFERRED EMBODIMENT

Figure 1:
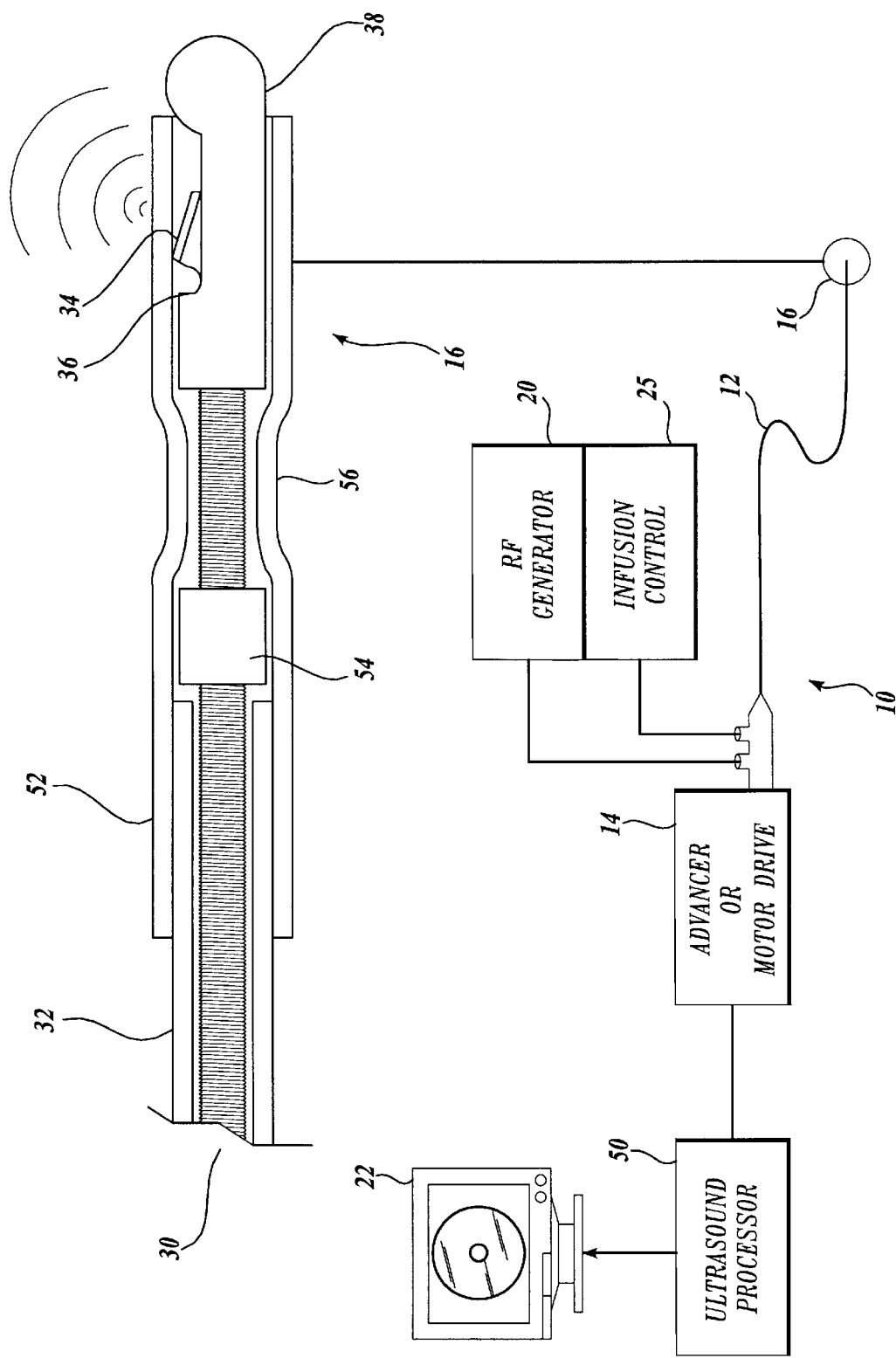
FIG. 1 illustrates a combination RF ablation and ultrasound catheter system for crossing total chronic occlusions according to one embodiment of the present invention.

FIG. 1 illustrates a combination ultrasound and RF ablation catheter system according to one embodiment of the present invention. The combination ultrasound and RF ablation system 10 includes a catheter 12 that is routed through a patient's vasculature to the point of a partial or total chronic occlusion that is restricting blood flow through a blood vessel (not shown). The catheter 12 is moved through the vasculature by a advancer 14 at the proximal end of the catheter 12. At the distal tip of the catheter 12 is an ultrasound transducer 34 that transmits ultrasound signals into the vessel tissue and receives corresponding echo signals. The echo signals are transmitted from the ultrasound transducer 34 to an ultrasound processor 20 that produces an image of the tissue surrounding the imaging head 16 on a video monitor 22.

To provide a 360° view of the vessel, the ultrasound transducer 34 is rotated by an electrically conductive driveshaft 30 that is rotated by the advancer 14 or motor drive at a rate of approximately 1,500–2,000 rpm. Surrounding the driveshaft 30 is a sheath 32 that prevents the driveshaft 30 from engaging the vessel walls. The details of the rotation ultrasound catheter 12 and advancer 14 are set forth in U.S. Pat. No. 5,000,185 which is assigned to Cardiovascular Imaging Systems, Inc. of Sunnyvale, Calif. and is herein incorporated by reference.

The ultrasound transducer 34 is integrated with a conductive electrode 38 that is secured to the distal end of the conductive driveshaft 30. According to one aspect of the present invention, the ultrasound transducer 34 is positioned in a window 36 on the side of the electrode such that ultrasound signals are transmitted to and echo signals are received from an area in the vessel that is adjacent the electrode 38 as well as a region that is just ahead or distal to the electrode 38.

In the presently preferred embodiment of the invention, an infusion control 25 at the proximal end of the catheter 12 pumps fluid such as saline, through the catheter 12 and around the ultrasound transducer 34 to clear blood cells away from the transducer. The saline acts as an acoustic coupling media between the transducer and the surrounding blood field.

In order to remove the occluding material from the vessel, the present invention also includes a radio frequency (RF) generator 50 that delivers RF energy to the electrode 38 at the distal end of the catheter 12. The RF energy is preferably transmitted through the conductive driveshaft 30 that rotates the ultrasound transducer 34 and the electrode 38. The sheath 32 that surrounds the driveshaft 30 is preferably non-conductive such that the RF energy enters the patient at the point of the electrode 38 exits the sheath 32. The RF energy vaporizes a portion of the occluding material in the vessel in order to revascularize the vessel. The RF energy is preferably returned to the RF generator 50 via an external patient pad (not shown) that serves as the return electrode. By utilizing the driveshaft 30 as the conductor for delivering the RF energy to the electrode 38, no additional wires are needed within the catheter 12. In the presently preferred embodiment of the invention, the driveshaft 30 is made of stainless steel. However, other conductive materials such as graphite or other metals could be used.

In the example shown in FIG. 1, the position of the electrode 38 with respect to the distal end of the surrounding sheath 32 is fixed by a sleeve 52, which is bonded to the distal end of the sheath 32. A cylindrical bearing 54 is secured around the driveshaft 30 proximal to the electrode 38. The sleeve 52 includes a tapered region 56 that lies between the cylindrical bearing 54 and the electrode 38. The ultrasound catheter cannot move forward because the cylindrical bearing 54 engages the tapered region 56 when the driveshaft 30 moved distally. Similarly, the electrode 38 cannot be withdrawn into the sheath 32 because the electrode 38 has a diameter that is larger than the diameter of the tapered region 56. The sleeve 52 is preferably made of a rubberized, sonically transparent material such as a heat shrink tubing. The tapered region is made by heating the tubing with a wrap of a current carrying wire.

Figure 2:
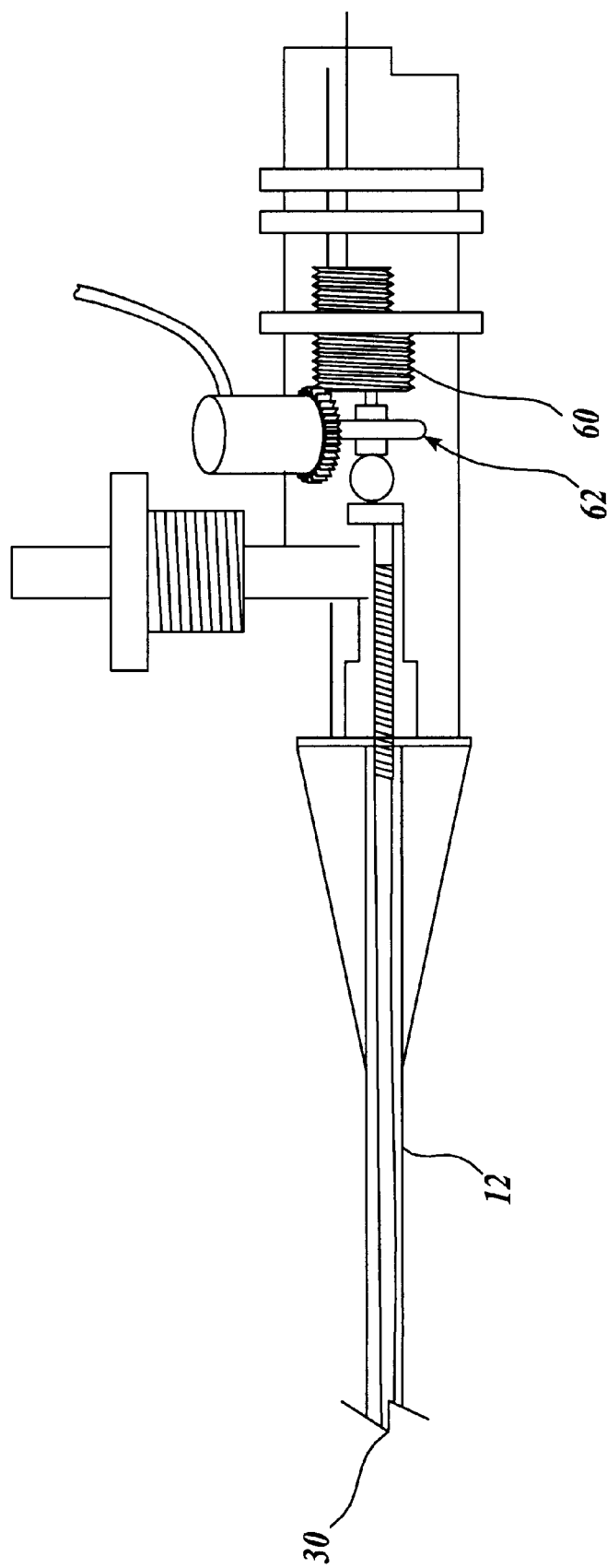
FIG. 2 illustrates a spring biased contact that applies RF ablation energy to a driveshaft that rotates an ultrasound transducer.

FIG. 2 illustrates a currently preferred method of coupling the RF ablation energy produced by the RF generator 50 to the conductive driveshaft that rotates the ultrasound transducer 34. At the proximal end of the catheter 12, is a slip ring coupler 60 that delivers ultrasound driving signals to and receives corresponding echo signals from the ultrasound transducer 34 that is positioned at the distal end of the catheter 12, as described in U.S. Pat. No. 5,000,185.

To deliver the RF ablation energy to the driveshaft 30, a spring contact 62 is coupled to the driveshaft 30 such that the spring contact 62 maintains an electrical connection as the driveshaft 30 is rotated. Upon activation of the RF generator 50 by the physician, RF ablation energy travels along the conductive driveshaft 30 to the electrode 38 at the distal tip of the catheter where the energy ablates occluding material in the vessel. By viewing an ultrasound image of the tissue on the monitor 22, the physician is able to keep the catheter 12 at the proper position in the vessel and minimize the risk of applying the RF ablation energy in the vicinity of the vessel wall.

Figure 3A:
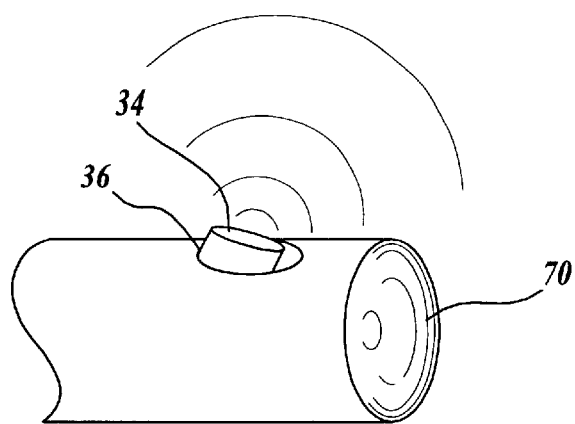
FIGS. 3A–3C illustrate a variety of RF electrode tip shapes according to other aspects of the present invention.
Figure 3B:
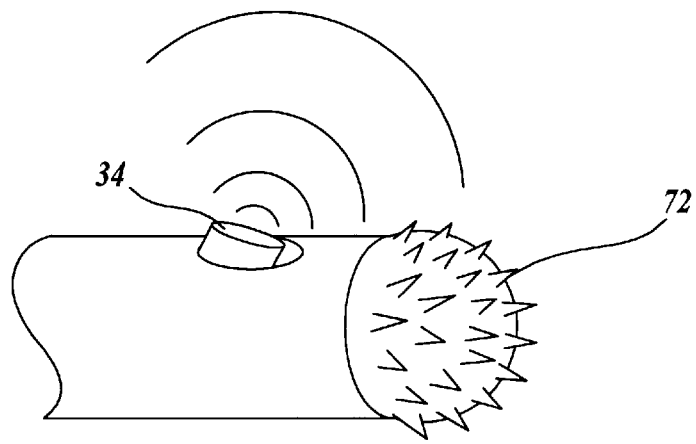

In order to control the delivery of RF ablation energy from the electrode 38 into the occluding material, a variety of electrode tip shapes may be used. In addition to the conventional hemispherical distal electrode tip, an electrode may include a distal tip having a concave surface 70 as shown in FIG. 3A. Alternatively, the electrode may include a distal tip having a hemispherical, convex distal tip 72 that is roughened as shown in FIG. 3B. The roughened surface creates an increased RF potential at the peaks of the roughened surface, which may uniformly distribute the area in which the RF ablation energy enters the occluding material in the patient's vessel.

Figure 3C:
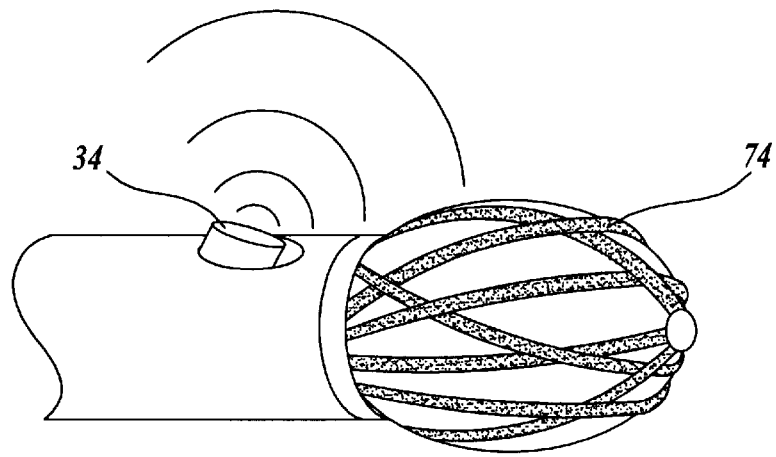

In yet another embodiment of the invention, the electrode includes an expandable distal tip 74 that is made of a pattern of intermeshed conductive wires as shown in FIG. 3C. When the electrode is extended out of a surrounding sheath, the wires revert to a pre-bent shape, thereby expanding the diameter of the electrode. The expanded electrode may be useful to create larger lumens in the occluding material.

FIG. 4 shows yet another embodiment of the present invention. Here, separate lumens of multi-lumen catheter 80 are used to route an ultrasound catheter 82 and a guidewire 84 between the proximal end of the catheter and the treatment site. In practice, the guidewire 84 is first advanced into the patient and the multi-lumen catheter 80 is routed over the guidewire 84 followed by the ultrasound catheter 82 in a different lumen of the multi-lumen catheter 80.

In this embodiment of the invention, the ultrasound catheter 82 is only used to obtain images of the patient's vessel. The RF generator 50 is connected to the guidewire 84, which is conductive, in order to deliver RF ablation energy to the occluding material at a point where the guidewire exits the multi-lumen catheter 80. In order to control the delivery of RF energy within the vessel, it is desirable that the length of the guidewire 84 that extends beyond the distal end of the multi-lumen catheter 80 be controlled. Therefore, the multi-lumen catheter 80 may include a marker band or other radio-opaque material near its distal end to allow the relative position of the distal end of the guidewire 84 and the distal end of the multi-lumen catheter 80 to be monitored.

In practice, the ultrasound catheter 82 is advanced in the vessel and an image of the tissue surrounding the ultrasound catheter 82 is obtained. After an image has been obtained, the ultrasound catheter 82 is retracted into the multi-lumen catheter 80 and the guidewire 84 is advanced out the distal end of the multi-lumen catheter 80 and RF ablation energy is applied to the guidewire, thereby ablating a portion of the occluding material in the vessel. The ultrasound catheter 82 is then extended into the newly created lumen and the process repeats until the vessel has been revascularized.

In order to further control the position of the ultrasound/RF ablation catheter in the vessel, a combination ultrasound/RF ablation catheter 98 may be routed in a steerable sheath 100 as shown in FIG. 5. The steerable sheath 100 preferably includes a steering wire 102 positioned along one wall of the sheath. A control mechanism 104 at the proximal end of the steerable sheath 100 is manipulated by the physician to retract or extend the steering wire 102, thereby causing deflection of the distal tip of the steerable sheath 100. The deflection of the distal tip is preferably adjusted such that the RF ablation/ultrasound catheter 98 is positioned in the center of the vessel in order to avoid applying the RF ablation energy too close to the vessel walls.

Figure 6:
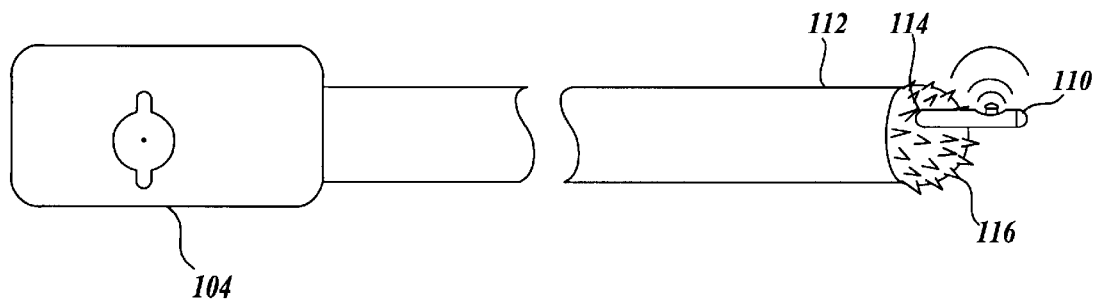
FIG. 6 illustrates an alternative embodiment of the present invention wherein a steerable sheath includes an electrode that delivers RF energy to an occlusion.

FIG. 6 shows yet another alternative embodiment of the present invention. Here, an ultrasound catheter 110 is routed through a steerable sheath 112 in order to position the ultrasound catheter 110 at a desired location in a patient's vessel. The ultrasound catheter 110 extends through a hole 114 at the distal end of the steerable sheath 112. In contrast to the embodiment shown in FIG. 5 that utilizes a combination ultrasound and RF ablation catheter, the catheter 110 is only used for obtaining ultrasound images of the vessel walls. To deliver the RF ablation energy, the steerable sheath 112 includes a conductive distal tip 116 having a hole 114 in it through which the ultrasound catheter 110 can be extended. RF energy is supplied to the conductive tip 116 to ablate occluding material in the vessel. The conductive tip 116 may be roughened as with the electrode tip shown in FIG. 3B to control the area in which ablation energy enters the occluding material.

In operation, the ultrasound catheter 110 can be advanced through the hole 114 in the distal tip 116 of the steerable sheath 112. Once an image of the tissue has been obtained, the ultrasound catheter 110 can be retracted into the steerable sheath 112 and RF ablation energy applied to the distal tip 116. The ultrasound catheter 110 is then inserted into the newly ablated area and the process continues.

Figure 7:
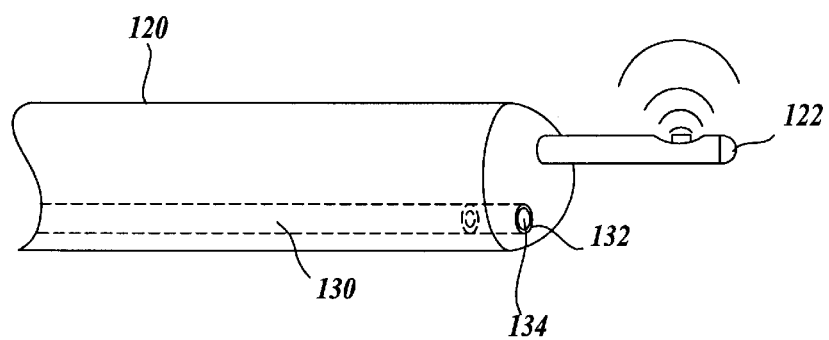
FIG. 7 illustrates yet another embodiment of the invention wherein a catheter includes a separate ultrasound catheter and RF ablation catheter.

FIG. 7 shows yet another alternative embodiment of the present invention. A multi-lumen catheter 120 includes a lumen through which an ultrasound catheter 122 can be routed. In addition, an aspiration/ablation catheter 130 can be used for ablating occluding material in the vessel and aspirating the ablated material. An aspiration/ablation catheter 130 is terminated with a cylindrical electrode 132 having a central lumen 134 in it that is connected to a vacuum source (not shown). RF energy is applied to the cylindrical electrode 132 to cut a core in the occluding material. Aspiration is applied to the aspiration catheter to remove ablated material.

As can be seen, the present invention is a simple catheter system that obtains images of a vessel and ablates occluding material such that a greater number of total chronic occlusions may be able to be treated without resorting to cardiac bypass surgery. Although the present embodiment of the invention utilizes a mechanically rotated ultrasound transducer, it will be appreciated that the ultrasound transducer could be rotated by hand to obtain a desired or 360° view of a vessel wall. This is a so-called "A" mode of operation. Alternatively, it is possible to use multiple transducers oriented in different directions so that a desired or 360° view of the vessel wall can be created with minimum rotation the ultrasound catheter.

The embodiments of the invention in which an exclusive property or privilege is claimed are defined as follows:

1. A system for treating occluded vessels, comprising:
    an ultrasound catheter including:
        at least one ultrasound transducer that directs ultrasonic energy into and receives corresponding echo signals from a vessel wall;
        a conductive driveshaft that rotates the at least one ultrasound transducer to obtain a 360° image of the vessel wall;
        an electrode coupled to the distal end of the conductive driveshaft; and
    an RF energy source that selectively applies RF ablation energy to the conductive driveshaft to deliver the RF ablation energy to the electrode.

2. The system of claim 1, wherein the at least one ultrasound transducer is fitted within the electrode and is positioned to direct ultrasound signals into and receive echo signals from a position in the vessel distal to the electrode.

3. The system of claim 1, wherein the electrode has a distal tip that is concave.

4. The system of claim 1, wherein the electrode has a distal tip that is hemispherical and roughened.

5. The system of claim 1, wherein the electrode has a distal tip that is expandable.

6. The system of claim 1, wherein the ultrasound catheter is routed through a steerable sheath.

7. A method of ablating an occlusion in a vessel, comprising:
    advancing a catheter into the vessel near the area of the occlusion;
    advancing a conductive driveshaft within the catheter, wherein the driveshaft rotates an imaging device for obtaining images of the occlusion and/or the vessel in the area near the occlusion, said drive shaft also having an electrode for delivery of ablation energy;
    rotating said drive shaft to obtain 360-degree images of said occlusion and/or said vessel; and
    applying ablation energy to said conductive drive shaft to be delivered to the occlusion by said electrode.

* * * * *